United States Patent [19]

Nelson et al.

[11] Patent Number: 5,138,083

[45] Date of Patent: Aug. 11, 1992

[54] METHODS OF PRODUCING ALPHA-ALKENYLALKYLSILANES

[75] Inventors: Gunner E. Nelson; John G. Loop, both of Baton Rouge, La.

[73] Assignee: Ethyl Corporation, Richmond, Va.

[21] Appl. No.: 695,411

[22] Filed: May 3, 1991

[51] Int. Cl.⁵ .............................................. C07F 7/08
[52] U.S. Cl. ..................................................... 556/478
[58] Field of Search ......................................... 556/478

[56] References Cited

U.S. PATENT DOCUMENTS 4,711,965  12/1987  Nelson ................................. 556/478
4,916,245   4/1990  Nelson ................................. 556/478

*Primary Examiner*—Paul F. Shaver
*Attorney, Agent, or Firm*—David E. LaRose

[57] ABSTRACT

Novel methods for producing alpha-alkenylalkylsilanes by reacting alkenylhalosilanes and organoalkalimetalaluminates have been discovered. For example, vinyltrichlorosilane and sodium tetraheylaluminate can be reacted to produce alpha-alkenyltrihexylsilane.

24 Claims, No Drawings

METHODS OF PRODUCING ALPHA-ALKENYLALKYLSILANES

BACKGROUND

Silahydrocarbons are attractive for use as high temperature hydraulic fluids and other uses, such as general lubricants. One type of compound useable as a silahydrocarbon, or as an intermediate to other silahydrocarbons, are alpha-alkenylalkylsilanes. Known methods for producing alpha-alkenylalkylsilanes include reactions involving organometallic reagents and hydrosilation, e.g. "Grignard-type" RMgBr reactions. For instance, see Paige, H. L.; Snyder, C. E.; and Chen, G. J.; "A Systematic Study of the Oxidative Stability of Silahydrocarbons by Pressure Differential Scanning Calorimetry," *LUBRICATION ENGINEERING* (April, 1990) pp. 263–267. There still exists a need for economical methods of producing alpha-alkenylalkylsilanes.

SUMMARY OF THE INVENTION

Novel methods for producing alpha-alkenylalkylsilanes by reacting alkenylhalosilanes and organoalkalimetalaluminates have been discovered. For example, vinyltrichlorosilane and sodium tetrahexylaluminate can be reacted to produce alpha-alkenyltri-hexylsilane.

DESCRIPTION OF THE PREFERRED EMBODIMENTS

Novel methods have been discovered for producing an alpha-alkenylalkylsilane comprising reacting an alkenylhalo-silane and an organoalkalimetalaluminate to produce said alpha-alkenylalkylsilane. Such result is unexpected inasmuch as vinyltrichlorosilane would be expected to react in an "ene" reaction with suitably disposed olefins to yield delta-alkenylsilanes.

The organoalkalimetalaluminates in the present invention can also be termed "alkali metal alkylaluminates". Such compounds can be represented by a general formula of $MAlR_4$ and will be further described hereinafter.

In the present invention, the alkenyl group of the alkenylhalosilane is a vinylhalosilane. Such vinylhalosilane can be represented by the formula $CH_2=CHSiH_nX_{3-n}$, wherein n is 0, 1 or 2, and X is a halogen atom. Preferably, the vinylhalo-silane contains at least two halogen atoms (i.e., $n=1$ or 0). More preferably, the vinylhalosilane is vinyltrihalosilane (i.e. $n=0$). Embodiments of the present invention can include mixtures of vinylhalosilanes. When hydrogen atoms are attached to the silicon atoms, reactions can occur in which the hydrogen atoms become replaced by hydrocarbon groups (e.g. the alkyl groups hereinafter described). More than one alkenyl group can be present. For instance, the alkenylhalosilane can be divinyldihalosilane.

The halogen atoms are each preferably independently selected from a group consisting of bromine, chlorine, fluorine and iodine atoms. For instance, when the alpha-alkenylhalo-silane is vinyltrihalosilane, the vinyltrihalosilane can be vinyltrichlorosilane, vinylfluorodichlorosilane, vinylchlorodifluorosilane, vinyltrifluorosilane, vinylbromodichlorosilane, vinyldibromoflurosilane or other similar compounds. More preferably, the halogen atoms are independently selected from a group consisting of chlorine or fluorine. Particularly preferred is vinyltrichlorosilane as the alkenylhalosilane. Mixtures of the different vinyltrihalosilanes also can be used.

Embodiments of the present invention also can include reactions wherein the alkenylhalosilane is an alpha-alkenylhaloalkylsilane. That is, one or more halogen or hydrogen atoms of the alpha-alkenylhalosilane is replaced by an alkyl group, e.g. $CH_2=CHSiH_nX_pR_{3-n-p}$, wherein n and p are each independently 0, 1 or 2 and the value of n +p is less than 3. An example is $CH_2=CHSiHClC_2H_5$. The alkyl groups preferably are normal, straight chain carbon groups, preferably having from one to about twenty carbons.

Preferably, the metal atom of the organoalkalimetalaluminate is selected from Group IA metals. More preferably, the Group IA metals are either lithium or sodium. The organoalkalimetalaluminum can be a mixture, such that two or more types of metal atoms are present, e.g. a mixture comprising $NaAlR_4$ and $LiAlR_4$, wherein R each are independently selected alkyl groups as hereinafter described. In a preferred embodiment the organoalkalimetalaluminate comprises a mixture of alkyllithiumaluminates and alkylsodiumaluminates in a respective molar ratio of from about 0.05:1 to about 0.25:1.

As stated hereinabove, the alkyl groups are independent; that is, each alkyl group can be the same or different in the number of carbons. Accordingly, each alkyl group of the organoalkalimetalaluminate independently comprises at least two carbon atoms. The maximum number of carbon atoms can be limited by the intended use, such as solubility limitations. Preferably, each alkyl group independently comprises from about two to about fifty carbon atoms. More preferably, each alkyl group independently comprises from about six to about fourteen carbon atoms. Each alkyl group independently can be either a straight or branched chain alkyl group.

Preferably, each alkyl group is a straight alkyl group. Examples of such straight alkyl groups include, but are not limited to ethyl, propyl, butyl, pentyl, hexyl, heptyl, octyl, nonyl, decyl, dodecyl, tetradecyl and others up to the maximum number of carbons atoms as specified hereinabove. All alkyl groups can be the same of different. For example, the organoalkalimetalaluminate can be $NaAl(C_6H_{13})_4$, $NaAl(C_6H_{13})_3(C_8H_{17})$, $NaAl(C_6H_{13})_2(C_8H_{17})_2$, $LiAl(C_6H_{13})(C_8H_{17})_3$ or other similar compounds.

Although pure alkyl groups (e.g. containing only aliphatic carbons and hydrogen) are preferred, at least one alkyl group can comprise a substituted carbon atom in which the substituting atom is selected from a group consisting of nitrogen, oxygen and sulfur atoms. Examples of such types of substituted (e.g. containing heteroatoms) alkyl groups include (—$CH_2CH_2OCH_2CH_2CH_3$) and (—$CH_2CH_2SCH_2CH_2CH_3$). Similarly, at least one alkyl group can comprise an aryl group, such as —$CH_2CH_2$-phenyl-$CH_3$. Such compounds can have useful antioxidative properties.

Solvents usable in the present invention can be any in which the reactants and products are suitably soluble and which does not produce undesired side reactions. Such solvents can be hydrocarbons such as alkanes, alkenes and aromatics. Preferred solvents approximate the saturated, straight chain nature of the alkyl groups of the reactants and products. For instance, when hexyl groups are present in the reactants, hexane or hexene can be used. Since more than one type of alkyl group can be present, a solvent mixture might be used. Preferably the solvent is a hydrocarbon solvent comprising molecules which comprise the same number of carbon atoms as at least one alkyl group of the organoalkalimetalaluminate.

Reaction temperatures should be sufficiently high to reasonably drive the reaction without causing undesired side reactions. Such temperatures can be above room temperatures, preferably, ranging from about 150° C. to about 210° C.

A preferred embodiment is a method of producing an alpha-alkenylsilane comprising reacting (a) an alpha-alkenylhalosilane having the formula $$CH_2=CHSiX_3$$

wherein each X is independently selected from a group consisting of bromine, chlorine and fluorine atoms, and (b) an organoalkalimetalaluminate mixture comprising organoalkalimetalaluminates having the formula $$MAlR_4$$

wherein each M independently is either a lithium or sodium atom and each R is selected from a group consisting of $R^1$, $R^2$, $R^3$, $R^4$ and $R^5$, each of which is independently (i.e., the same or different) an alkyl group having the formula $$-C_nH_{2n+1},$$

wherein n is an integer ranging from two to about fifty,
to produce a reaction product comprising said alpha-alkenylsilane having the formula $$R^5-CH=CH-SiR_3,$$

wherein $P^5$ is one of said R groups in $MAlR_4$.

The alkenylhalosilane $CH_2=CHSiX_3$ can be one type or a mixture of alkenylhalosilanes, such that the halogen composition for each alkenylhalosilane can vary within the prescribed limitation. Preferably, the alkenylhalosilane $CH_2=CHSiX_3$ is $CH_2=CHSiCl_3$. Also, preferably the organoalkalimetalaluminate mixture is a mixture of $LiAlR_4$ and $NaAlR_4$ is in a respective ratio of about 0.05:1 to about 0.25:1 more preferably about 0.10:1, and each R is independently an alkyl group of about fourteen carbon atoms, preferably having a straight chain structure.

The following experiments illustrate embodiments of the invention, but are not intended to limit the scope of the invention herein.

EXPERIMENT 1

Working in a glovebox with a nitrogen atmosphere under anhydrous conditions, $NaAl(C_6H_{13})_4$ (0.499 mol) as an unisolated reaction product in 1-hexene with one-tenth molar percent $LiAl(C_6H_{13})_4$ was added into a dry, clean, nitrogen purged Parr autoclave. Admixed with the aluminate was vinyltrichlorosilane (0.554 mol). This aluminate was present in a 15% molar excess.

The autoclave was sealed and then inserted into a Parr heating jacket and controller. The following heating profile was programmed into the heat controller for the jacket:

| Set Point 0 | 25° C. |
|---|---|
| Time 1 | 20 minutes |
| Temp 1 | 40° C. |
| Time 2 | 1 hour |
| Temp 2 | 40° C. |
| Time 3 | 30 minutes |
| Temp 3 | 125° C. |
| Time 4 | 1 hour |
| Temp 4 | 125° C. |
| Time 5 | 30 minutes |
| Temp 5 | 190° C. |
| Time 6 | 5 hours |
| Temp 6 | 190° C. |
| Time 7 | 25 minutes |
| Temp 7 | 15° C. |

The stirrer was started and agitation was done throughout the entire reaction program.

After the bomb cooled down overnight with continuous stirring, the autoclave was reinserted into the dry box where the reaction product obtained was transferred to a one liter round bottom vessel with a drop stem on the bottom. This round bottom vessel was then placed over a 2000 ml round bottom flask containing 800 mls of 25% caustic (NaOH solution) and fitted with a stirrer. The set-up had been flushed with nitrogen several minutes before the reaction product was placed over it. With a generous purge of nitrogen the reaction product was slowly dripped into the stirring caustic. The addition of the reaction product warmed the 2 liter round bottom flask as the excess aluminate was hydrolyzed. The reaction product was allowed to hydrolyze with the rapidly stirring caustic for approximately 30 minutes. After hydrolysis, the reaction product was washed several times with water to bring the pH of the wash water to neutral. After the washing, the product was dried over $MgSO_4/Al_2O_3$ powders overnight.

The dried product was filtered away from the $MgSO_4/Al_2O_3$ powders and isolated by distillation under reduced pressures. Initial analysis of the product was done by gas chromatography which showed that the reaction product was 83.6 unit percent $CH_3-(CH_2-)_5-CH=CH-Si-(C_6H_{13})_3$. The product was also identified by NMR and GC-MS analyses as this unsaturated product.

EXPERIMENT 2

A hexylaluminate, $NaAl(C_6H_{13})_4$, was prepared with one-tenth molar percent $LiAl(C_6H_{13})_4$ in 1-hexene. This aluminate was then distilled to remove the 1-hexene. In its place dodecane (300 mL) was added to the aluminate in a nitrogen atmosphere dry box. Distillation was performed under slight vacuum. Distillation removed 75% by weight of the 1-hexene. The aluminate was returned to the dry box. An analysis to determine aluminum concentration was performed and the aluminum was found to be 2.84 wt %.

After determining the concentration of the aluminate, the aluminate (0.611 mol) was transferred to a dry, clean, nitrogen purged Parr autoclave. Admixed with the aluminate was vinyl-trichloro silane (0.679 mol). This left the aluminate in 15 molar percent excess.

The bomb was sealed and the contents reacted using the same temperature profile as stated for experiment 1. The reaction product was worked up in the same fashion as experiment 1. The product, however, was found to be a mixture of the unsaturated $CH_3-(CH_2-)_5-CH=CH-Si-(C_6H_{13})_3$ species and the saturated species $(C_8H_{17})-Si-(C_6H_{13})_3$. The ratio of the two species was approximately 2:1 in favor of the unsaturated species.

The two species were isolated together by distillation under vacuum, and NMR and GC-MS analyses confirmed the two structures.

EXPERIMENT 3

For trial number three, another $NaAl(C_6H_{13})_4$ aluminate was prepared. This aluminate was distilled as was the aluminate in experiment 2, except that heptane (400 mL) and hexene (200 mL) were added as replacement solvent and chaser for the distillation removal of excess 1-hexene present with the aluminate.

The distillation removed over 450 mL of solvent, thereby removing at least 95% of the 230 milliliters of excess 1-hexene. This distilled aluminate was analyzed for its Al concentration and the concentration was found to be 3.94 wt %, a very concentrated aluminate.

Some of the aluminate (583.7 mmol) was added to a one-liter Parr autoclave along with dry heptane as additional solvent. Admixed with the distilled aluminate was vinyl-trichlorosilane (648.6 mmol). This left the aluminate in a 15 molar percent excess in the autoclave.

The reactants were heated using the same temperature profile as used in the reaction of the first two trials. The reaction product was worked up in a similar manner and the product, $CH_3-(CH_2)_5-CH=CH-Si-(C_6H_{13})_3$, was isolated by vacuum distillations.

A GC analysis showed that the one major product of this reaction was the unsaturated species listed above. NMR and GC-MS analyses confirmed the product's structure.

EXPERIMENT 4

The rest of the aluminate product for experiment 3 was used in experiment 4. The aluminate (169 mmol) was added to a dry, clean, nitrogen purged autoclave. Admixed with the distilled aluminate was vinyl-trichloro silane (219.5 mmol). This molar ratio left the aluminate as a 2% excess in the reaction.

The reactants were reacted in the following abbreviated reaction profile which was programmed to the Parr heating jacket controller:

| | |
|---|---|
| Set Point 0 | 25° C. |
| Time 1 | 30 minutes |
| Temp 1 | 125° C. |
| Time 2 | 1 hour |
| Temp 2 | 125° C. |
| Time 3 | 30 minutes |
| Temp 3 | 190° C. |
| Time 4 | 4 hours |
| Temp 4 | 190° C. |
| Time 5 | 25 minutes |
| Temp 5 | 15° C. |

The reactants were reacted under this temperature ramps and dwell set-up with constant stirring. After cooling overnight the reaction product was worked up using the same techniques as described for the other trials. A GC of the reaction product showed that the major product of the reaction was the unsaturated $CH_3-(CH_2)_5-CH=CH-Si-(C_6H_{13})_3$ species.

What is claimed is:

1. A method of producing an alpha-alkenylalkylsilane comprising reacting an alpha-alkenylhalosilane and an organo-alkalimetalaluminate to produce said alpha-alkenylalkylsilane.

2. The method of claim 1 wherein the alpha-alkenylhalosilane is a vinylhalosilane.

3. The method of claim 2 wherein the vinylhalosilane contains at least two halogen atoms.

4. The method of claim 3 wherein the vinylhalosilane is vinyltrihalosilane.

5. The method of claim 3 wherein the vinylhalosilane is divinyldihalosilane.

6. The method of claim 2 wherein the halogen atoms are each independently selected from a group consisting of bromine, chlorine, fluorine and iodine atoms.

7. The method of claim 6 wherein the halogen atoms are independently selected from a group consisting of chlorine or fluorine atoms.

8. The method of claim 7 wherein the alpha-alkenylhalosilane is vinyltrichlorosilane.

9. The method of claim 1 wherein the alpha-alkenylhalosilane is an alpha-alkenylhaloalkylsilane.

10. The method of claim 1 wherein the metal atom of the organoalkalimetalaluminate is selected from Group IA atoms.

11. The method of claim 10 wherein the Group IA atoms are either lithium or sodium or a mixture thereof.

12. The method of claim 11 wherein the organoalkalimetalaluminate comprises a mixture of alkyllithium-aluminates and alkylsodiumaluminates in a respective molar ratio of from about 0.05:1 to about 0.25:1.

13. The method of claim 10 wherein each alkyl group of the organoalkalimetalaluminate independently comprises at least two carbon atoms.

14. The method of claim 13 wherein each alkyl group independently comprises from about two to about fifty carbon atoms.

15. The method of claim 14 wherein each alkyl group independently comprises from about six to about fourteen carbon atoms.

16. The method of claim 10 wherein each alkyl group independently is either a straight or branched alkyl group.

17. The method of claim 16 wherein each alkyl group is a straight alkyl group.

18. The method of claim 16 wherein at least one alkyl group comprises a substituted carbon atom in which the substituting atom is selected from a group consisting of nitrogen, oxygen and sulfur atoms.

19. The method of claim 10 wherein at least one alkyl group comprises an aryl group.

20. The method of claim 1 performed in a hydrocarbon solvent comprising molecules which comprise the same number of carbon atoms as at least one alkyl group of the organoalkalimetalaluminate.

21. The method of claim 1 performed at a temperature ranging from about 150° C. to about 210° C.

22. A method of producing an alpha-alkenylsilane comprising reacting (a) an alpha-alkenylhalosilane having the formula $CH_2=CHSiX_3$ wherein each X is independently selected from a group consisting of bromine, chlorine and fluorine atoms, and (b) an organoalkalimetalaluminate mixture comprising organoalkalimetalaluminates having the formula

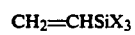

$MAlR_4$ wherein each M independently is either a lithium or sodium atom and each R is selected from a group consisting of $R^1$, $R^2$, $R^3$, $R^4$ and $R^5$, each of which is independently (i.e., the same or different) an alkyl group having the formula $$-C_nH_{2n+1},$$

wherein n is an integer ranging from two to about fifty, to produce a reaction product comprising said alpha-alkenylsilane having the formula $$R^5-CH=CH-SiR_3,$$

wherein $R^5$ is one of said R groups in $MAlR_4$.

23. The method of claim 22 wherein $CH_2=CHSiX_3$ is $CH_2=CHSiCl_3$.

24. The method of claim 22 wherein the organoalkalimetalaluminate mixture is a mixture of $LiAlR_4$ and $NaAlR_4$ in a respective ratio of about 0.10:1 and each R is independently an alkyl group of about fourteen carbon atoms.

* * * * *